US009194820B2

(12) United States Patent
Nishimoto et al.

(10) Patent No.: US 9,194,820 B2
(45) Date of Patent: Nov. 24, 2015

(54) METHOD FOR MANUFACTURING A TURBINE ROTOR

(71) Applicant: MITSUBISHI HEAVY INDUSTRIES, LTD., Tokyo (JP)

(72) Inventors: Shin Nishimoto, Tokyo (JP); Makoto Tanaka, Tokyo (JP); Kenji Kawasaki, Tokyo (JP); Hiroyuki Endo, Tokyo (JP); Kentaro Uchiyama, Tokyo (JP); Yoshinobu Koori, Yokohama (JP)

(73) Assignee: MITSUBISHI HITACHI POWER SYSTEMS, LTD., Kanagawa (JP)

( * ) Notice: Subject to any disclaimer, the term of this patent is extended or adjusted under 35 U.S.C. 154(b) by 140 days.

(21) Appl. No.: 13/837,487

(22) Filed: Mar. 15, 2013

(65) Prior Publication Data

US 2014/0153693 A1 Jun. 5, 2014

(30) Foreign Application Priority Data

Dec. 5, 2012 (JP) ................................. 2012-266779

(51) Int. Cl.
*G01N 23/04* (2006.01)
*G01N 23/18* (2006.01)
*F01D 5/02* (2006.01)
*F01D 5/06* (2006.01)

(52) U.S. Cl.
CPC ................ *G01N 23/04* (2013.01); *F01D 5/063* (2013.01); *G01N 2223/629* (2013.01)

(58) Field of Classification Search
CPC ............. G01N 23/04; G01N 2223/629; B23K 2201/001; F01D 5/063
See application file for complete search history.

(56) References Cited

U.S. PATENT DOCUMENTS 6,152,697 A * 11/2000 Konishi et al. ............ 416/213 R
2002/0190099 A1 * 12/2002 Nakamura et al. ............ 228/104
(Continued)

FOREIGN PATENT DOCUMENTS

JP 9-108883 4/1997
JP 2001-47232 2/2001
(Continued)

OTHER PUBLICATIONS

International Search Report issued Jun. 18, 2013 in corresponding International Application No. PCT/JP2013/059091.
(Continued)

*Primary Examiner* — Glen Kao
*Assistant Examiner* — Dani Fox
(74) *Attorney, Agent, or Firm* — Wenderoth, Lind & Ponack, L.L.P.

(57) ABSTRACT

An inspection method for a welded joint formed between a pair of base metals (10, 20) with a groove part (12, 22) and an abutment face (14, 24) being formed on a joint surface Wc between the pair of base metals. The method includes the steps of: forming a recessed groove (32) opening to a surface of the base metals in advance at one end of the abutment face; irradiating the joint surface Wc with an X-ray generator (34) placed on a groove part formation side (an exterior space O side) toward the joint surface Wc after at least one pass $P_1$ of build-up welding is performed on the groove parts (12, 22); and determining the presence or absence of incomplete penetration in the welded joint part W based on an image formed on a photosensitive film (42) by radiation penetrating the joint surface Wc.

12 Claims, 7 Drawing Sheets

(56) References Cited

U.S. PATENT DOCUMENTS

2011/0076153 A1* 3/2011 Imano et al. ............. 416/244 R
2011/0198318 A1* 8/2011 Silvia et al. .................... 219/75

FOREIGN PATENT DOCUMENTS

JP  2010-201507  9/2010
JP  2011-177790  9/2011

OTHER PUBLICATIONS

Patent Cooperation Treaty (PCT) International Preliminary Report on Patentability issued in International Application No. PCT/JP2013/059091 on Jun. 18, 2015.

Patent Cooperation Treaty (PCT) International Preliminary Report on Patentability issued in International Application No. PCT/JP2013/059091 on Jun. 9, 2015.

* cited by examiner

ENLARGED VIEW OF SECTION A

METHOD FOR MANUFACTURING A TURBINE ROTOR

BACKGROUND OF THE INVENTION

1. Technical Field

The present invention relates to a method of non-destructively inspecting a welded joint for incomplete penetration using radiation.

2. Description of the Related Art

In a rotor of a steam turbine, in association with the trend of using high temperature steam, a high-temperature section subjected to high temperature steam is made of material different from a low-temperature section subjected to low temperature steam so that each section is made of material appropriate for its environment and the sections are connected to each other by welding. For instance, the high-temperature section is made of high heat resisting steel, whereas the low-temperature section is made of low alloy steel. FIG. 8 illustrates a common structure of a steam turbine. In FIG. 8, the steam turbine 1 is configured such that a plurality of split hollow disks 7 are fitted together between split hollow disks 5 having support shafts 3 and cylindrical ends and that abutment portions of adjacent two of the split hollow disks 5, 7 are connected at a welded joint part W. In this manner, in the steam turbine 1 manufactured by welding the split hollow disks 5, 7 together, it is important to inspect a welding state of the welded joint part W. Further, as illustrated in FIG. 1, the steam turbine 1 has an interior space I formed therein.

FIG. 9A and FIG. 9B illustrate a welding method of related art for the welded joint part W. In FIG. 9A, the base metal 100 and the base metal 200 constitute the hollow disks that are made of different materials and on joint surfaces of the base metals 100, 200, groove parts 102, 202 and abutment faces 104, 204 are respectively formed. As illustrated in FIG. 9A, the groove parts 102, 202 are formed on a side that faces an exterior space O and the abutment faces 104, 204 are formed on a side facing the interior space I. A welding torch 300 is positioned between the groove part 102 and the groove part 202 from the exterior space O.

Next, as illustrated in FIG. 9B, the abutment faces 104, 204 are melted together and also build-up welding is performed on the groove parts 102, 202 one pass at a time using the welding torch 300. After performing the build-up welding, a penetration part M formed between the abutment faces 104, 204 needs to be inspected for lack of penetration. However, the penetration part M cannot be visually checked from the exterior space O. Thus, an inspection hole 106 is formed in the base metal 100 (or the base metal 200) to insert a borescope (not shown) into the interior space I through the inspection hole 106 from the exterior space O in the direction of arrow a. If the penetration part M is accessible, the borescope is inserted toward the penetration part M from the interior space I in the axial direction of the interior space I (direction of arrow b). Then, using the borescope, the penetration part M is visually checked for complete penetration. This visual inspection is preferably performed immediately after welding the first pass (a root pass) to make it easier to repair the part in case that lack of penetration is found.

It is described in JP 09-108883 A to perform the above inspection on the welded joint part of a steam turbine rotor. Further, JP 09-108883 A also describes that an X-ray source is inserted into the interior space I through the inspection hole and then a radiographic test of the welded joint part is carried out to inspect the welding state of the welded joint part. Further, it is described in JP 2010-201507 A to visually monitor the welding part, in the case of welding a rotor of a steam turbine or the like, by means of a video system integrated in a welding torch. Furthermore, JP 2011-177790 A describes that in the case of welding the steam turbine rotor or the like, the joint surface is formed with a groove and an abutment face and the abutment faces have complementary shapes to form a protrusion and a recess for orienting the joint surfaces of two base metal pieces.

SUMMARY OF THE INVENTION

1. Technical Problem

In the inspection methods of the related art, it is necessary to form the inspection hole or the interior space I so that the borescope can be inserted to the welded joint part W from the exterior space O. However, the interior space I does not always exist. Also, by making the inspection hole in the base metal, the strength of the base metal is deteriorated and thus, structural design taking into account the strength of the base metal around the inspection hole is required. Further, there is a concern that foreign objects such as steam enter the base metal through the inspection hole, which may affect operation of a device such as a steam turbine formed by the base metals.

As described in JP 09-108883 A, in the radiographic test using the X-ray source inserted in the inspection hole, the remaining state of the abutment face is checked using a radiographic image projected on a photosensitive film. Based on this, it is checked whether or not penetration of the abutment face is incomplete. However, the abutment face is hard to form an image on the photosensitive film. Further, the image captured on the photosensitive film is of the part disposed on the side farther from an X-ray generator and thus it is difficult to check presence or absence of the abutment face based on the image on the photosensitive film.

In view of the above issues of the related art, it is an object of the present invention to attain an inspection method for a welded joint, which enables inspection of the abutment face disposed where it cannot be visually inspected, without making an inspection hole in the base metal.

2. Solution to the Problem

To achieve the above object, an inspection method for a welded joint according to the present invention is an inspection method for a welded joint formed between a pair of base metals with a groove part and an abutment face being formed on a joint surface between the pair of base metals. The inspection method comprises steps of:

forming a recessed groove opening to a surface of the base metal in advance at one end of the abutment face;

irradiating the joint surface from a groove part formation side after at least one pass of build-up welding is performed on the groove part; and determining presence or absence of incomplete penetration in the welded joint based on an image formed on a photosensitive film by radiation penetrating the joint surface.

In the present invention, the recessed groove is formed in advance and the step of irradiating the joint surface is performed after welding. Then, presence or absence of the recessed groove is determined based on the image formed on the photosensitive film. The presence or absence of the recessed groove can be clearly confirmed, unlike the abutment face. If the recessed groove is confirmed, it is determined there is incomplete penetration. If the recessed groove is not confirmed, it is determined that the abutment faces are penetrated. As a result, it is no longer necessary to provide the inspection hole and the above-mentioned issues regarding the inspection hole can be solved. Further, the irradiation step may be performed immediately after welding the first pass (a root pass) so that it is easier to repair the part in case that incomplete penetration is found.

In the present invention, the recessed groove preferably has a cross section area whose dimension has a lower limit so that the recessed groove is distinguishable using the image obtained in the determining step and an upper limit so that the recessed groove is fillable with the at least one pass of build-up welding. As a result, presence or absence of the recessed groove after welding can be confirmed by irradiating the joint surface and the recessed groove can be filled by build-up welding. Therefore, the adverse effect on strength, etc. of the base metal can be eliminated.

A shape of the recessed groove in cross section may be arc, preferably rectangular, so that the image obtained by irradiation can be clearly formed on the film. In the case where the recessed groove has a rectangular shape in cross section, the recessed groove has, for example, an opening width of 0.3 mm or more to 0.5 mm or less and a depth of 0.2 mm or more to 1.0 mm or less to satisfy the above conditions.

In the present invention, the recessed groove is formed preferably on the joint surface of only one of the pair of base metals. This makes it easier to form the recessed groove. Further, on the joint surface, a protrusion and a recess are preferably formed adjacent to the recessed groove, the protrusion and the recess being configured to complementarily fit to each other. This makes it easier to position the joint surfaces of the pair of base materials with respect to each other.

In such a case where the pair of base metals has a hollow cylindrical shape and are welded to each other in an axial direction via the joint surfaces, with application of the present invention to this, the presence or absence of incomplete penetration in the abutment face formed facing the interior space of a hollow cylindrical shape can be inspected without making the inspection hole. For instance, by applying the present invention to a welded rotor for a turbine which is formed by the hollow cylindrical bodies welded to one another in the axial direction via the joint surfaces, the presence or absence of incomplete penetration in the abutment face formed in the joint surface can be inspected without making the inspection hole.

3. Advantageous Effects

According to the present invention, it is possible to check the presence or absence of incomplete penetration in the abutment faces of the welded joint surfaces where they cannot be visually checked directly, without making the inspection hole in the base metal. This saves the extra work of making the inspection hole and also prevents a reduction in the strength of the base metal. Further, the interior space of the base metal is maintained tightly sealed.

DETAILED DESCRIPTION OF THE INVENTION

The present invention will now be described in detail using embodiments shown in the accompanying drawings. It is intended, however, that unless particularly specified in these embodiments, dimensions, materials, and shapes of components, their relative positions and the like shall be interpreted as illustrative only and not limitative of the scope of the present invention.

First Embodiment

Figure 1:
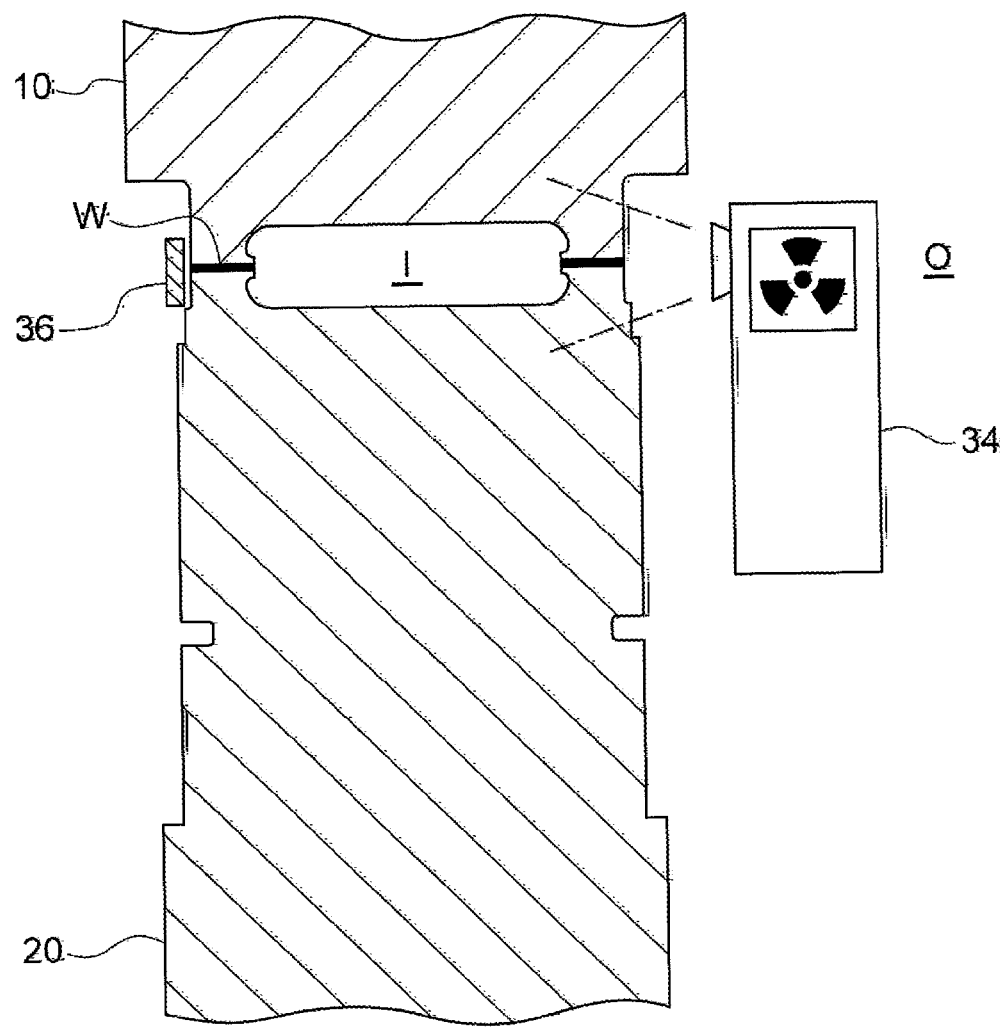
FIG. 1 is a cross-sectional view of a welded joint part in relation to a first embodiment of the present invention.
Figure 2:
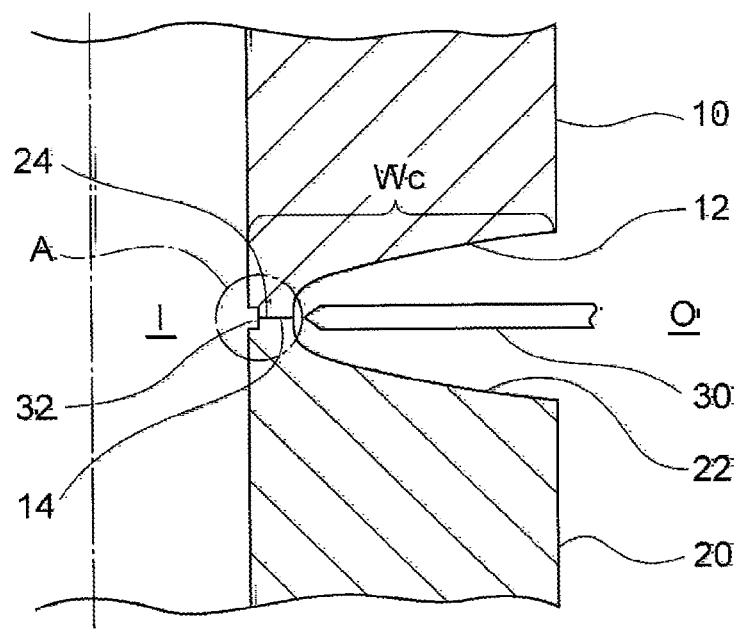
FIG. 2 is an enlarged cross-sectional view of a part of FIG. 1.
Figure 3:
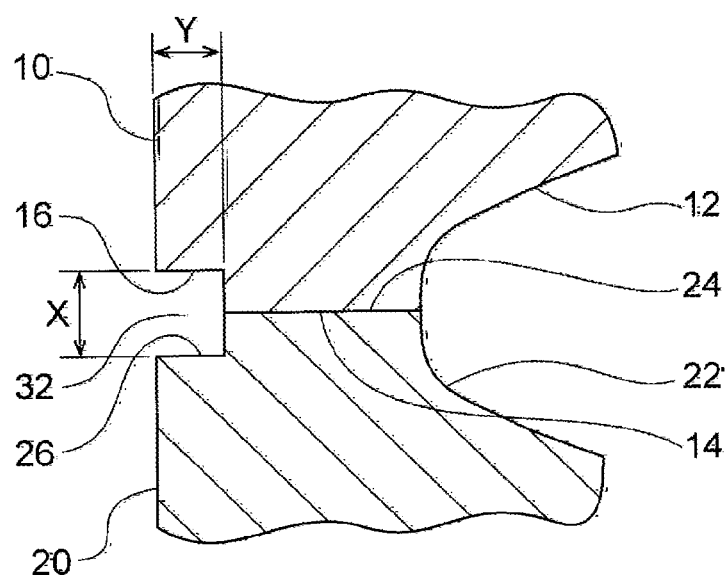
FIG. 3 is an enlarged cross-sectional view of section A of FIG. 2.

A first embodiment of the present invention is explained with reference to FIG. 1 to FIG. 4. FIG. 1 illustrates the state where split hollow disks 10, 20 forming a steam turbine rotor are welded together at a welded joint part W. The steam turbine rotor is formed by a plurality of split hollow disks including the split hollow disks 10, 20 that are welded together in the axial direction. Inside the welded joint part W, an interior space I is formed. FIG. 2 and FIG. 3 show a joint surface Wc before welding.

In FIG. 2 and FIG. 3, the joint surface Wc has groove parts 12, 22 formed on an exterior space O side and abutment faces 14, 24 formed on the interior space I side. The abutment faces 14, 24 are in contact with each other.

As illustrated in FIG. 3, a circular recessed groove 32 opening to the interior space I is formed at one end of the abutment faces 14, 24 in the circumferential direction of the split hollow disks 10, 20. The end of the abutment faces 14, 24, where the recessed groove 32 is formed, is on an opposite side of the abutment faces 14, 24 relative to the groove parts 12, 22. The recessed groove 32 is formed by a rectangular notch 16 formed in the abutment face 14 of the split hollow disk 10 and another rectangular notch 26 formed in the abutment face 24 of the split hollow disk 20, that are disposed facing each other. The recessed groove 32 has a symmetrical shape with respect to the abutment faces 14, 24. In this embodiment, the recessed groove 32 has an opening width X in the axial direction, X being 0.3 mm to 0.5 mm and a depth Y being 0.2 mm to 1.0 mm.

As illustrated in FIG. 2, the joint surface Wc is welded by placing a welding torch 30 in a groove formed by the groove parts 12, 22 from the exterior space O, directing the welding torch 30 toward the abutment faces 14, 24, and then rotating the split hollow disks 10, 20 in a state in which the split hollow disks 10, 20 are positioned with respect to each other. In this state, build-up welding is performed by the welding torch 30 on the groove formed by the groove parts 12, 22. By laying one pass (a root pass), a penetration part is formed in the abutment faces 14, 24 and the recessed groove 32 is filled. Next, ten to twenty passes of build-up welding are performed to fill the groove formed by the groove parts 12, 22.

After laying one pass, an X-ray generator 34 is placed in the exterior space O to check the presence or absence of incomplete penetration in the abutment faces 14, 24 as illustrated in FIG. 1. Further, a high-temperature film cassette 36 is attached to outer circumferential surfaces of the split hollow disks 10, 20 which are 180° out of phase with the X-ray generator 34, at a position to extend over the welded joint part W.

Figure 4:
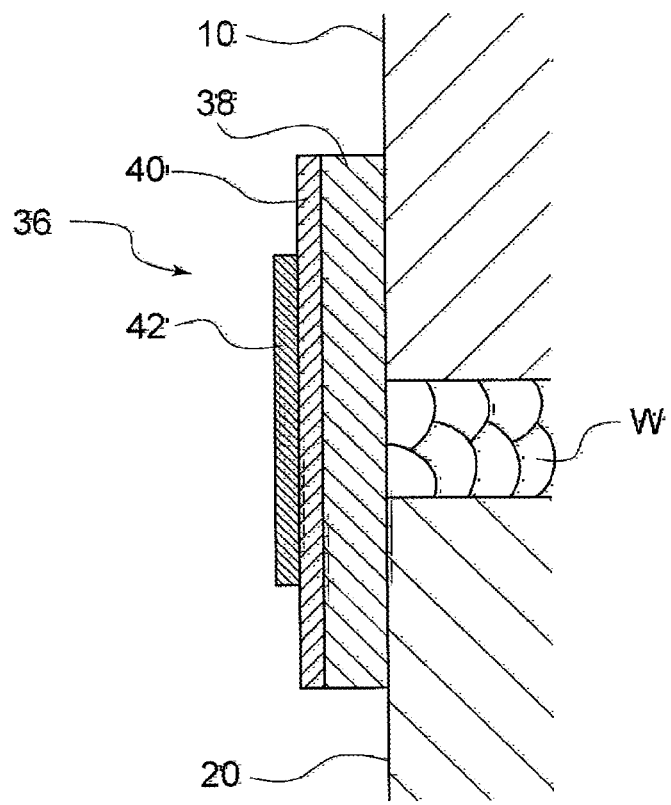
FIG. 4 is a cross-sectional view of a photosensitive film used in the first embodiment.

FIG. 4 illustrates the configuration of the high-temperature film cassette 36. The high-temperature film cassette 36 includes a Teflon™ plate 38, a heat-insulating plate 40 made of heat insulating material, and a photosensitive film 42 on which radiation having passed through the welded joint part W is exposed. The Teflon™ plate 38, the heat-insulating plate 40 and the photosensitive film 42 are stacked in this order from a side nearer to the welded joint part W so as to form the high-temperature film cassette 36. When irradiating a specimen, the radiation penetrates the specimen and gradually weakens due to interaction with the specimen. In the case of a welded part, the radiation penetrates well in a region with defects such as blowholes compared to a region without defects. As a result, the region with defects such as blowholes is detected as a dark image on the photosensitive film 42.

In this configuration, X-rays are emitted toward the welded joint part W from the X-ray generator 34 and the photosensitive film 42 is exposed to the X-rays that have penetrated the welded joint part W to form an image on the photosensitive film 42. The image formed on the photosensitive film 42 is the welded joint part W on a side farthest from the X-ray generator 34. Thus, if there is incomplete penetration in the abutment faces 14, 24, an image of the recessed groove 32 is formed clearly on the photosensitive film 42.

According to this embodiment, when there is incomplete penetration in the abutment faces 14, 24, the recessed groove 32 is shown on the photosensitive film 42 clearly as a dark image. Thus, it is possible to precisely acknowledge the presence or absence of incomplete penetration in the abutment faces 14, 24. Therefore, it is no longer necessary to drill an inspection hole in the split hollow disks 10, 20. This saves the extra work of forming the inspection hole and also avoids a decline in the strength of the split hollow disks 10, 20.

Further, the interior space I can be maintained airtight, so that steam can be prevented from entering the interior space I and affecting the operation of the steam turbine or deteriorating the operation efficiency. Further, as the cross sectional area of the recessed groove 32 is rectangular, the shape of the recessed groove 32 can be clearly formed on the photosensitive film 42. Further, as the cross sectional area of the recessed groove 32 has the above-described dimensions, the image of the recessed groove 32 can be formed distinctly on the photosensitive film 42 and the recessed groove 32 can be surely filled with one pass of build-up welding. Furthermore, the welded joint part W is irradiated after one pass of build-up welding. This makes it easier to repair the part after confirming incomplete penetration.

Second Embodiment

Figure 5:
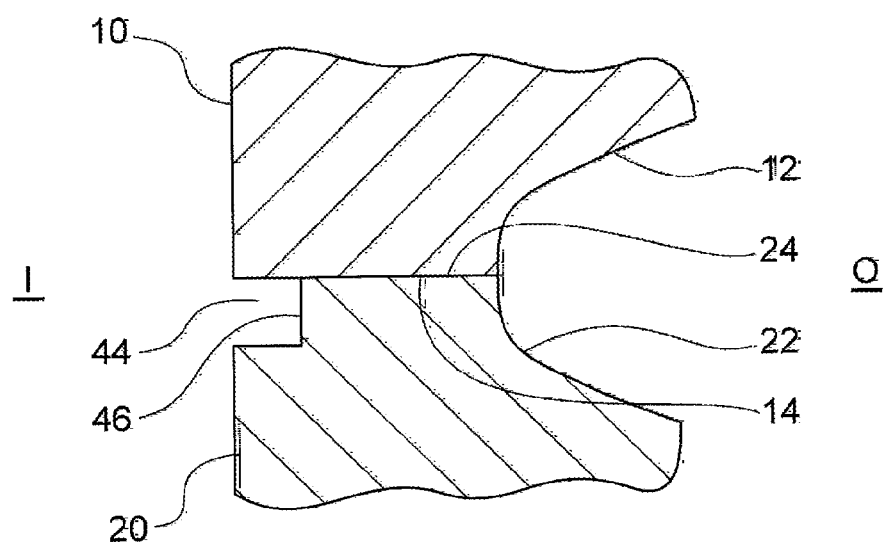
FIG. 5 is a cross-sectional view of a welded joint part in relation to a second embodiment of the present invention.

Next, a second embodiment of the present invention is explained in reference to FIG. 5. In this embodiment, similarly to the first embodiment, a circular recessed groove 44 opening to the interior space I is formed at one end of the abutment faces 14, 24 in the circumferential direction of the split hollow disks 10, 20. The end of the abutment faces 14, 24, where the recessed groove 44 is formed, is on an opposite side of the abutment faces 14, 24 relative to the groove parts 12, 22. The recessed groove 44 is formed by arranging the split hollow disk 10 and a rectangular notch 46 formed only in the abutment face 24 of the split hollow disk 20 to face each other. The rest of the configuration is the same as that of the first embodiment. According to this embodiment, the recessed groove 44 can be formed by machining only the abutment face 24 and thus formation of the recessed groove 44 is easy.

Third Embodiment

Next, a third embodiment of the present invention is explained in reference to FIG. 6A, FIG. 6B, FIG. 7A, FIG. 7B, and FIG. 7C. In this embodiment, similarly to the second embodiment, the recessed groove 44 opening to the interior space I is formed by arranging the split hollow disk 10 and the rectangular notch 46 formed only in the abutment face 24 of the split hollow disk 20 to face each other. In addition to the recessed groove 44, a protrusion 48 and a protrusion 50 are formed adjacent to the recessed groove 44 behind the recessed groove 44 (the exterior space O side) in the abutment faces 24, 14 of the split hollow disks 20, 10, respectively. These protrusions 48, 50 have shapes that complementarily fit to each other.

Figure 6A:
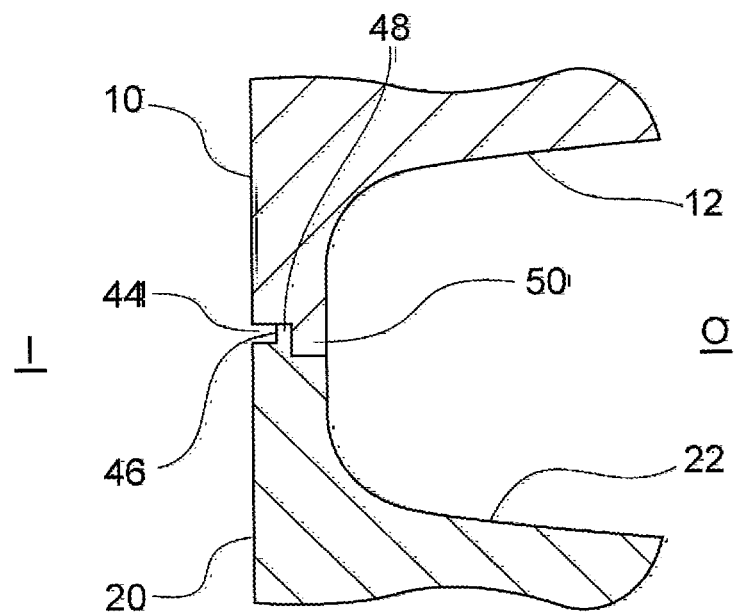
FIG. 6A is a cross-sectional view of a pre-welding joint surface which is the joint surface before welding in relation to a third embodiment of the present invention.
Figure 6B:
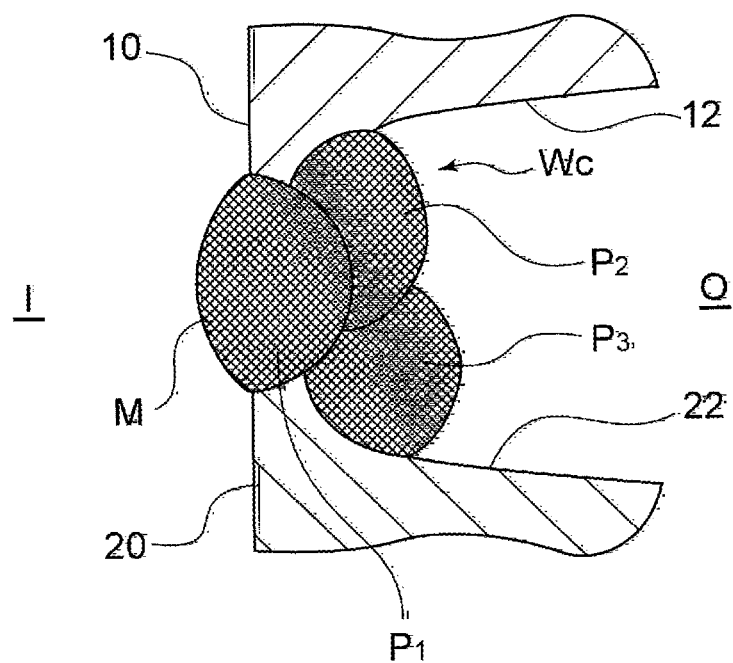
FIG. 6B is a cross-sectional view of a post-welding joint surface which is a joint surface after welding in relation to the third embodiment of the present invention.
Figure 7A:
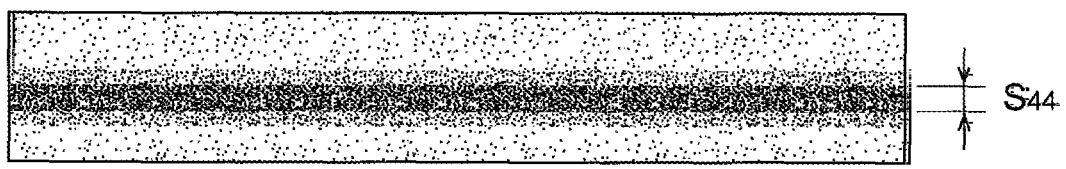
FIG. 7A is an image of the pre-welding joint surface captured on a photosensitive film in relation to the third embodiment.
Figure 7B:
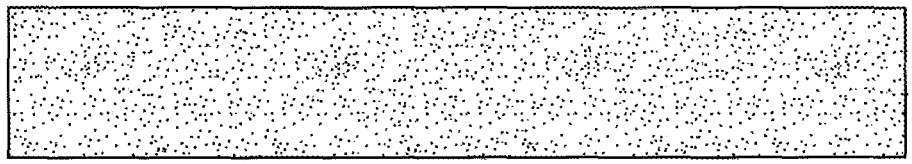
FIG. 7B is an image of the post-welding joint surface captured on the photosensitive film in relation to the third embodiment.

FIG. 6B illustrates the joint surface Wc after the first pass $P_1$, the second pass $P_2$ and the third pass $P_3$ of build-up welding are performed. By the first pass $P_1$, the penetration part M is formed in the abutment faces to fill the recessed groove 44. FIG. 7A is an image of the pre-welding joint part W captured on the photosensitive film 42. FIG. 7B is an actual image of the welded joint part W captured on the photosensitive film 42 after the first pass of build-up welding is performed. In FIG. 7A, the image $S_{44}$ of the recessed groove 44 is clearly shown. In contrast, in FIG. 7B, no image is formed on the photosensitive film 42, and thus it can be seen that the penetration part M is formed in the abutment faces and the recessed groove 44 is successfully filled.

Figure 7C:
FIG. 7C is an image of a pre-welding joint surface in which a recessed groove is not formed (Comparison Example).
Figure 8:
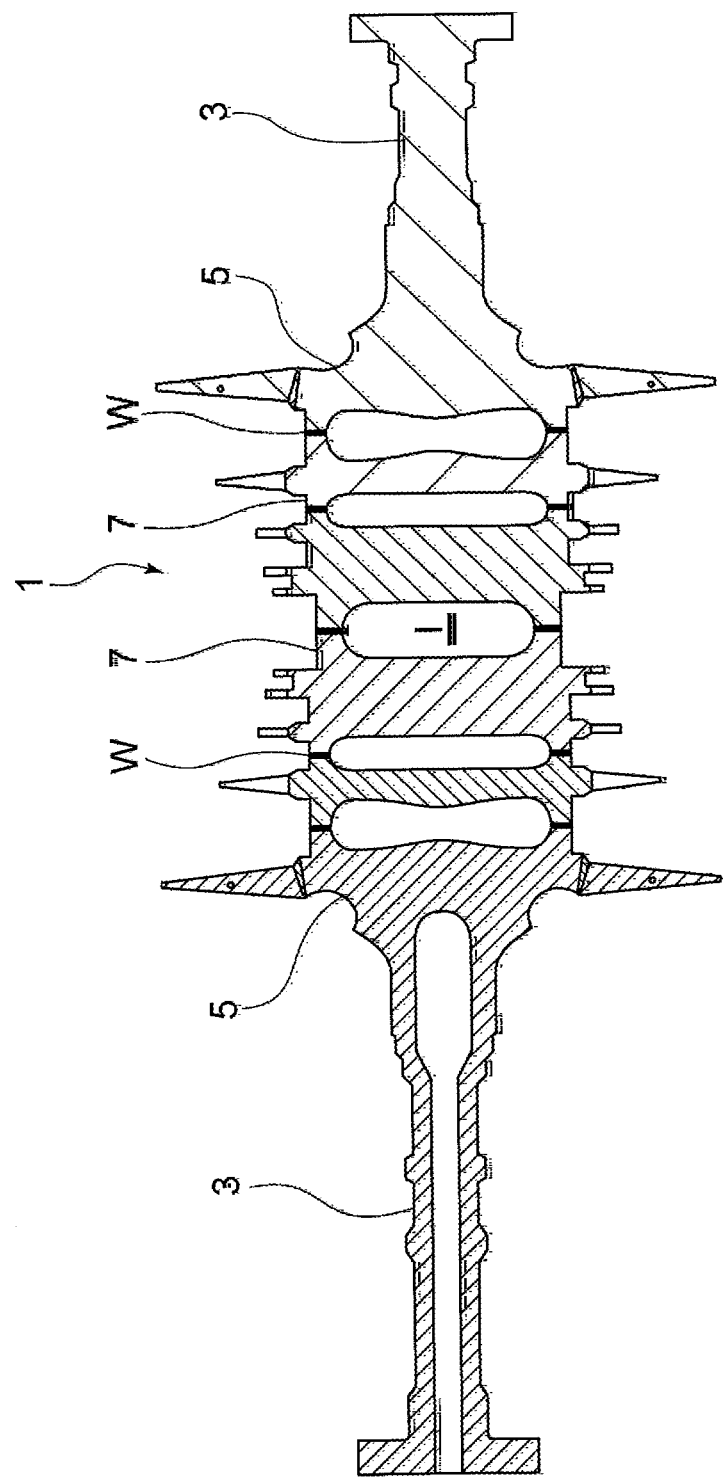
FIG. 8 is a cross-sectional view of a steam turbine rotor taken from the front.
Figure 9A:
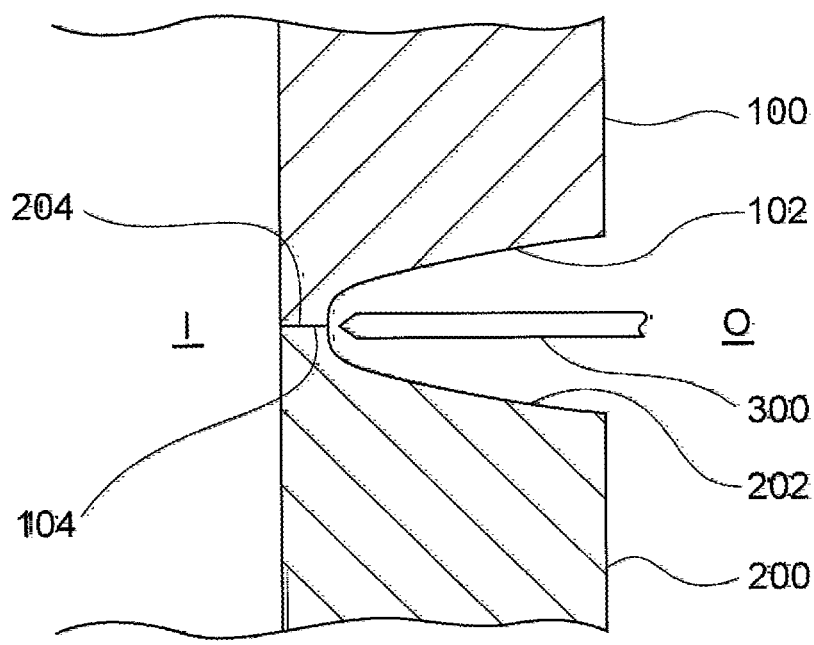
FIG. 9A is a cross-sectional view of a pre-welding joint surface according to a conventional welding method.
Figure 9B:
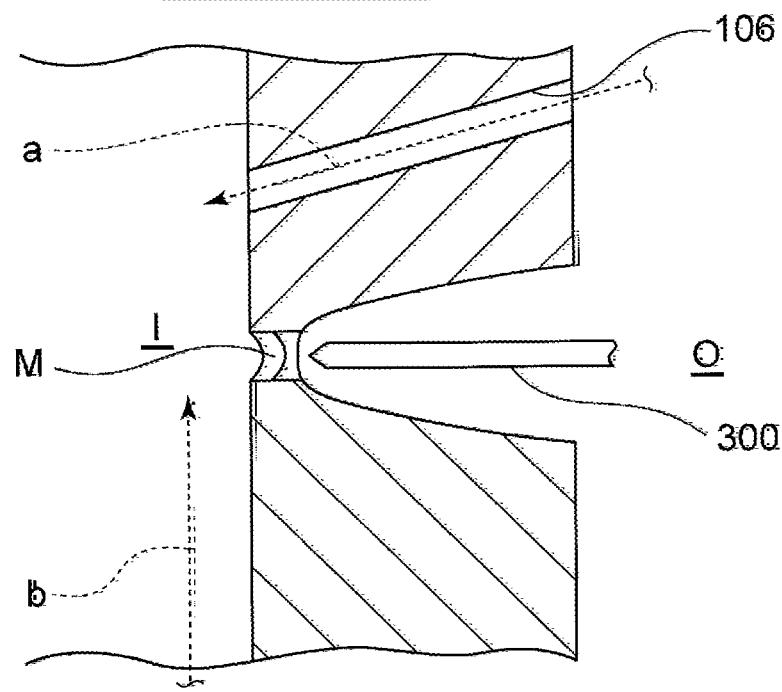
FIG. 9B is a cross-sectional view of a joint surface on which one pass is welded according to the conventional welding method.

FIG. 7C is an image of the joint part W shown as a comparison example. In this comparison example, the welded joint part W is not formed with the recessed groove 44 and the image of the welded joint part W is formed on the photosensitive film 42. In FIG. 7C, the line of the abutment face is vaguely confirmed. However, it is hard to distinguish from the rest. This makes it difficult to determine whether or not the penetration part M is formed normally after the first pass of build-up welding.

According to this embodiment, the same function effects as in the second embodiment can be obtained. Further, as the protrusions 48, 50 that complementarily fit to each other are formed in the abutment face of the split hollow disks 10, 20, and thus the sealing effect of the interior space I in the welded joint part W can be enhanced. Furthermore, as the protrusions 48, 50 are formed, it is easier to position the split hollow disks 10, 20 with respect to each other when welding.

According to the present invention, inspection of the welded joint part can be performed on the abutment faces of the welded joint surfaces located where they cannot be visually inspected, without making an inspection hole in a base metal.

REFERENCE SIGNS LIST

1 Steam turbine
3 Support shaft 5, 7, 10, 20 Split hollow disk
12, 22, 102, 202 Groove part
14, 24, 104, 204 Abutment face
16, 26, 46 Notch
30, 300 Welding torch
32, 44 Recessed groove
34 X-ray generator
36 High-temperature film cassette
38 Teflon™ plate
40 Heat-insulating plate
42 Photosensitive film
48, 50 Protrusion
100, 200 Base metal
106 Inspection hole
I Interior space
M Penetration part
Exterior space
$P_1$, $P_2$, $P_3$ Build-up welding
W Welded joint part
$W_C$ Joint surface

The invention claimed is:

1. A method for manufacturing a turbine rotor, the method comprising the steps of:
    forming a recessed groove on at least one of a first disk and a second disk adapted to a turbine rotor, each of the first disk and the second disk having a body supportable for a rotor blade and a circular part protruding from the body toward an axial direction, each of the circular parts of the first and second disks having a joint surface at a tip end of the circular part in the axial direction, the joint surface having an abutment face and a groove part, the joint surfaces of the first disk and the second disk being capable of contacting each other, the groove parts of the first disk and the second disk being capable of forming an outer circumferential groove outside of the abutment faces in a radial direction, the recessed groove being formed at a tip end side and an inner circumferential side on at least one of the first disk and the second disk so as to extend along a circumferential direction of the circular part;
    first-layer welding the abutment faces to each other through the outer circumferential groove so as to form a penetration part;
    imaging by x-ray radiation from outside of the penetration part in the radial direction of the circular part so as to form an image on a photosensitive film by x-ray radiation penetrating the penetration part after the first-layer welding step;
    determining the presence or absence of incomplete penetration in the penetration part based on the image obtained in the step of imaging;
    second-layer welding the groove parts to each other around the penetration part when an absence of incomplete penetration is determined in the determining step; and
    repairing the penetration part when the presence of incomplete penetration is determined in the determining step.

2. The method for manufacturing a turbine rotor according to claim 1, the method further comprising the steps of:
    forming a first protrusion part and a second protrusion part, the first protrusion part protruding in the axial direction so as to form a tier on the abutment face of the circular part of the first disk, the second protrusion part protruding in the axial direction so as to form a tier on the abutment face of the circular part of the second disk, and having a diameter smaller than the first protrusion part; and
    fitting the first protrusion part and the second protrusion part to each other concentrically before the first-layer welding step.

3. The method for manufacturing a turbine rotor according to claim 2, wherein the recessed groove is formed only on the circular part of the second disk, and the recessed groove is located inside the second protrusion part in the radial direction.

4. The method for manufacturing a turbine rotor according to claim 1, wherein the recessed groove has a cross section area whose dimension is set such that the presence of the recessed groove is recognizable in the determining step when the first-layer welding step results in failure and such that the recessed groove is fillable by first-layer welding step when the first-layer welding step results in success.

5. The method for manufacturing a turbine rotor according to claim 2, wherein the recessed groove has a cross section area whose dimension is set such that the presence of the recessed groove is recognizable in the determining step when the step of first-layer welding results in failure and such that the recessed groove is fillable by the first-layer welding step when the first-layer welding step results in success.

6. The method for manufacturing a turbine rotor according to claim 3, wherein the recessed groove has a cross section area whose dimension is set such that the presence of the recessed groove is recognizable in the determining step when the first-layer welding step results in failure and such that the recessed groove is fillable by the first-layer welding step when the first-layer welding step results in success.

7. A method for manufacturing a turbine rotor, the method comprising the steps of:
    providing a first disk and a second disk adapted to a turbine rotor, each of the first disk and the second disk having a body supportable for a rotor blade and a circular part protruding from the body toward an axial direction, each of the circular parts of the first and second disks having a joint surface at a tip end of the circular part in the axial direction, the joint surface having an abutment face and a groove part, the joint surfaces of the first disk and the second disk being capable of contacting each other, the groove parts of the first disk and the second disk being capable of forming an outer circumferential groove outside of the abutment faces in a radial direction, a recessed groove being formed at a tip end side and an inner circumferential side on at least one of the first disk and the second disk so as to extend along a circumferential direction of the circular part;
    first-layer welding the abutment faces to each other through the outer circumferential groove so as to form a penetration part;
    imaging by x-ray radiation from outside of the penetration part in the radial direction of the circular part so as to form an image on a photosensitive film by x-ray radiation penetrating the penetration part after the first-layer welding step;
    determining the presence or absence of incomplete penetration in the penetration part based on the image obtained in the step of imaging;
    second-layer welding the groove parts to each other around the penetration part when an absence of incomplete penetration is determined in the determining step; and
    repairing the penetration part when the presence of incomplete penetration is determined in the determining step.

8. The method for manufacturing a turbine rotor according to claim 7, the method further comprising the steps of:
    forming a first protrusion part and a second protrusion part, the first protrusion part protruding in the axial direction so as to form a tier on the abutment face of the circular part of the first disk, the second protrusion part protruding in the axial direction so as to form a tier on the abutment face of the circular part of the second disk, and having a diameter smaller than the first protrusion part; and fitting the first protrusion part and the second protrusion part to each other concentrically before the first-layer welding step.

9. The method for manufacturing a turbine rotor according to claim 8, wherein the recessed groove is formed only on the circular part of the second disk, and the recessed groove is located inside the second protrusion part in the radial direction.

10. The method for manufacturing a turbine rotor according to claim 7, wherein the recessed groove has a cross section area whose dimension is set such that the presence of the recessed groove is recognizable in the determining step when the first-layer welding step results in failure and such that the recessed groove is fillable by the first-layer welding step when the first-layer welding step results in success.

11. The method for manufacturing a turbine rotor according to claim 8, wherein the recessed groove has a cross section area whose dimension is set such that the presence of the recessed groove is recognizable in the determining step when the step of first-layer welding results in failure and such that the recessed groove is fillable by the first-layer welding step when the first-layer welding step results in success.

12. The method for manufacturing a turbine rotor according to claim 9, wherein the recessed groove has a cross section area whose dimension is set such that the presence of the recessed groove is recognizable in the determining step when the first-layer welding step results in failure and such that the recessed groove is fillable by the first-layer welding step when the first-layer welding step results in success.

* * * * *